United States Patent [19]

Lévêque et al.

[11] Patent Number: 4,616,933

[45] Date of Patent: Oct. 14, 1986

[54] PROCESS AND APPARATUS FOR MAKING A NUMERICAL DETERMINATION OF THE COLOR, OR OF A CHANGE IN COLOR, OF AN OBJECT

[75] Inventors: Jean-Luc M. Lévêque, Montfermeil; Gilbert J. Gras, Aulnay-Sous-Bois, both of France

[73] Assignee: L'Oreal, Paris, France

[21] Appl. No.: 593,882

[22] Filed: Mar. 27, 1984

Related U.S. Application Data

[63] Continuation-in-part of Ser. No. 186,325, Sep. 11, 1980, abandoned.

[30] Foreign Application Priority Data

Sep. 13, 1979 [FR] France .............................. 79 22881

[51] Int. Cl.⁴ .......................... G01J 3/51; G01N 21/55
[52] U.S. Cl. .................................. 356/416; 250/227; 356/445
[58] Field of Search .............................. 356/445–448, 356/402, 408, 416, 418, 425; 250/227

[56] References Cited

U.S. PATENT DOCUMENTS

| | | | |
|---|---|---|---|
| 3,327,584 | 6/1967 | Kissinger | 356/448 |
| 3,743,429 | 7/1973 | Kawai | 356/416 |
| 4,241,738 | 12/1980 | Lübbers et al. | 356/418 |
| 4,278,353 | 7/1981 | Ostermayer, Jr. | 356/448 |

FOREIGN PATENT DOCUMENTS 2404845 4/1979 France .

OTHER PUBLICATIONS

"Ein berührungsloses Remissions Spektral Photometer für den Bereich von 300 bis 1100 nm" by Kölmel & Kasten, Feinwerktechnik & Messtechnik, vol. 86, No. 6, Aug./Sep. 1978, pp. 273–274.

Product Report "Fiber Optics Scanner Checks Needles" Control Engineering, Sep. 1973, vol. 20, #9, p. 56.

*Primary Examiner*—Vincent P. McGraw
*Attorney, Agent, or Firm*—Cushman, Darby & Cushman

[57] ABSTRACT

A coaxial optical fiber bundle assembly (Reference No. 6 in the following Specification and Drawing), carrying emitted light from a light source and received light which has been returned by an object illuminated from said light source, is moved towards the object (Reference No.: 7) to cause the intensity of the received light, as detected by a photo transistor in light emitter-receiver unit (Reference No.: 1), to attain a maximum value which is amplified and held as a display on digital voltmeter (Reference No.: 11). Comparison of the held value with the corresponding held maximum value resulting from a similar determination made of either a different object of the same object after a color change therein or thereof can thus be made on a numerical basis.

17 Claims, 4 Drawing Figures

PROCESS AND APPARATUS FOR MAKING A NUMERICAL DETERMINATION OF THE COLOR, OR OF A CHANGE IN COLOR, OF AN OBJECT

HISTORY OF THE APPLICATION

The instant Application is a Continuation-In-Part of the co-pending but herewith-abandoned application for U.S. Letters Patent made by the present inventors and entitled "Process and Apparatus for Making a Numerical Determination of the Colour, or of a Colour Change, of an Object" having Ser. No. 06/186,325 which was filed Sept. 11, 1980 and is now abandoned, along this line and pursuant to 35 U.S.C. 119, priority of and for the invention disclosed and claimed in the instant application is to be found in French Patent Application No. 79.22881 which was filed in France on Sept. 13, 1979.

BACKGROUND OF THE INVENTION

A number of techniques and apparatus have been known and used for investigating and numerically determining the color and/or a change in the color of various objects, including living tissue.

These are typically represented and indicated by the disclosures and teachings in several and various references, including by way of more specific illustration: an Article entitled "Ein berührungsloses Remissionssektralphotometer für den Bereich von 300 bis 100 nm" by K. Kölmel and K. Kasten appearing at Pages 273–274 in FEINWERTECHNIK & MESSTECHNIK, Vol. 86, No. 6 for August/September, 1978; a Product Report entitled "Fiber Optics Scanner Checks Needles" appearing at Page 56 of "CONTROL ENGINEERING" for September, 1973, Vol. 20, No. 9; U.S. Pat. Nos. 3,327,584; 3,743,429; 4,241,738; and 4,278,353, as well as French Pat. No.: 2,404,845.

In the typical instance, the apparatus employed requires actual contact with the object being investigated.

Nonetheless and notwithstanding, nothing in prior art seems nor appears to realistically concern itself with the determination and allocation of numerical value(s) to objects being investigated without requirements for actual contact—with many advantageous results and possibilities forthcoming therewith—for simply and readily making numerical determinations of the color, or of a color change, of an object as in the way so crucially indigenous as is in the present contribution to the art.

DESCRIPTION OF THE INVENTION

The present invention relates to an apparatus and a process for carrying out a numerical determination of the color, or of a color change, of an object including and of frequent great practicability one that is formed of living animal and human tissue.

Uniquely and of particular value and advantage in and for many desired and important applications in use and practice therewith and thereof, the process and apparatus of the present invention do not require any contact with any particular object being investigated.

It is known and it is oftentimes not only desirable but much wanted and needed and even necessary to allocate a numerical value to the color, or the color change of an object. Usually, the observation of an object by the human eye makes it possible to give qualitative information. But, this natural technique has two drawbacks. For one thing and in illustration of the indicated deficiencies, if the qualitative information is converted into quantitative date by an observer, the numerical value depends considerably on the judgement of the particular observer. This, as is readily appreciable, may vary from and between one observer to and with reference to another. Moreover, the human eye has difficulties in its capabilities of observation to allocate an indication corresponding strictly to the state of a restricted zone without taking into account the color impression supplied by the surroundings of the observed zone. Of course, the surroundings of the object being observed are always taken into consideration. Thus and as a consequence of this, the results of the qualitative observation of a zone under consideration depend largely on the contrasts supplied by the surrounding zones.

The above-noted phenomenon is particularly evident when one is examining, for instance, the state of redness of human skin. This is particularly so in situations following solar radiation with possible attendant sunburn of the skin surface being examined and observed for color change(s) therein. The observation is affected not only by the intensity of the lighting, but also by the background color of the irradiated skin and by the extent of the contrast thus effected between the normal skin and the reddened skin.

It is, moreover, known that any apparatus permitting the numerical determination of an object's color should be able to function without any absolute necessity of making actual physical contact with the object in the zone being investigated. In fact, certain objects to be observed may be moving, or hot, or radioactive. Therefore, and for obvious reasons, it is generally preferred in such situations that the object whose color or color change is being measured must not come into contact with the apparatus. Other objects may change their color if they are subjected to pressure as can readily occur, for instance, in the cases with color measurement(s) of irradiated skin where contact pressure invariably produces whitening due to closing of the thereunder-pressured capillaries. This color change is also the case with liquid crystals which change color according to some given pressure to which they are subjected.

Now then, in the present state of the technology associated with the art with which the present invention is concerned, numerical determination of a color is obtained by successively illuminating the object under investigation by luminous emissions corresponding to different wave lengths and measuring in each case the light returned by the object by way of reflection and diffusion towards a receiver. This technique essentially requires the maintenance of a strictly determined distance between the measuring apparatus and the object subjected to observation. Thus and unavoidably, when soft materials are being observed, it is necessary to bring the materials into contact with a glass plate or slide. It follows that a pressure influence during such procedures which, even though of small magnitude, is not zero, is exerted on the object(s) to be observed. Consequently, this method is neither truly suitable nor entirely satisfactory in the case of materials which change color according to pressure influences exerted thereon and/or of those which are moving, hot, radioactive or the like and so forth.

Moreover, according to the heretofore known art, the result of the measurement depends as has been indicated on the surrounding lighting. In order to become independent thereof, it is not possible to use a pulsed source. This is due to the basic reason that, in order to obtain a sufficient quantity of light reflected and diffused by the object, it is mandatory to use a powerful source.

It can thus be readily seen and appreciated that the present state of technology does not provide an apparatus or technique which is capable of numerically recording a color or a color modification of an object in a simple and reproducible manner without any necessity of actual contact with the said object under observation.

The primary and most fundamental object of the present invention is to provide a process and an apparatus facilitating the numerical determination of a color, or a color change, of an object wherein there is no absolute requirement of contact with the said object under investigation.

Strictly speaking, the apparatus does not make it possible to obtain an absolute numerical measurement corresponding to a color. Notwithstanding, it does make it possible to make a numerical determination of a color or a color change, which determination can be compared with determinations made by using other similar apparatus. With such an apparatus, it is possible by way of one particular illustration to study the effects of vasoconstrictors by examining the whitening of a human skin. It is also possible, as another instance of what may be done, to study the extent of an erythema affecting a skin zone by comparing the measurement obtained on the said zone with a corresponding measurement obtained on a normal skin zone.

Moreover and as a yet further example of the advantageous capabilities and results inherent in practice of the present invention, one may first exert pressure on a reddened skin to close the capillaries and to whiten the skin zone concerned, and then release the applied pressure in order to enable excellently informative study of the kinetics of the return of the skin to its original color.

Apparatus according to the invention thus finds a great number of applications with all of this being achievable with utmost attractiveness thereabout since operation of the involved apparatus and practice of the present invention is extremely simple.

Accordingly, one aspect of the present invention provides apparatus for making a numerical determination of the color, or of a color change, of an object. The contemplated apparatus comprises: a source of light to irradiate the object undergoing observation and investigation; a photo transducer to receiver using said detector circuit, and displaying the output of said detector circuit using said display unit.

The important implementing principle of the invention lies in: the sending of a luminous emission onto the object to be investigated; receiving the light returned by the object; and then determining the maximum value of the reception as the receiving surface of the object subjected to the luminous emission is approached. When the emitting and receiving surfaces are the ends of optical fiber bundles, the intensity of the light retransmitted by the object generally passes through a maximum value if the two surfaces of the object are simultaneously brought near each other. The distance corresponding to the attainment of this maximum value only depends on the geometry of the receiver system. Therefore, if it is the said maximum value itself which is determined, the measurement of the retransmitted light is always effected at the same distance from the object. The result so realizable is thus independent of any constraint imposed by the heretofore known apparatus as is employed in present-day technology in the field of the instant invention.

The measurement assembly may, if desired, have a spectral sensitivity corresponding to the sensitivity of the human eye. It is thus possible to effect correlations between the measurements effected and direct visual observations. If the filter used in the embodimentation of the present apparatus that is employed allows a light to be emitted having a pick up the light returned by the object: optical fiber receiver means to direct the light returned by the object to the said photo transducer, the said optical fiber receiver means having a displaceable end which is disposed substantially perpendicularly to the object being investigated and in order to facilitate obtention of the desired determination; optical fiber emitter means adapted to direct the emission of said light source to a said object being investigated, with said optical fiber emitter means and optical fiber receiver means being fixed together for conjoint movement towards and away from a said given object being investigated; a detection circuit for determining the value of the maximum of the signal supplied by the photo receiver during the displacement of the said end of the optical fiber receiver means; and a display unit responsive to said detection circuit for displaying information according to the determination that is being accomplished and made.

Another aspect of the invention provides a process for making a numerical determination of the color, or of a change in color, of a given object under investigation which process compromises: taking an apparatus according to the first aspect of the invention as disclosed and explained in the immediate foregoing; moving said coaxial ends of said first and second optical fiber bundles towards said object while receiving the light from said light source returned from the said object; processing the output signal of said photo wave length corresponding to the object's color; whereupon and whereby the object will return a maximum quantity of light to the receiver.

It is readily comprehensible that the greater the difference of the object's color from the medium wave length of the light emission used, the more the quantity of light returned to the receiver by the object will be reduced. It is thus easily perceivable that the intensity of the maximum value of the output signal from the photo transducer essentially depends on the color of the object under investigation for a luminous emission having any given spectral characteristics. If one examines, with the same light emission, two differently colored zones of the same object or the same zone of the object after its color has been modified and if the results of the two measurements are compared, one obtains a numerical indication of the color modification of the object which is practically independent of any particular light emission that may be employed.

In a preferred embodiment of the apparatus, the said first and second optical fiber bundles have their ends coaxial and in the same plane substantially parallel to the object. It is possible in actual practice of the invention to cause the said ends to approach the object under investigation in a course that is substantially perpendicular to the object in order to effect the required determination. The receiver, from the object being investigated and color evaluated, picks up from the object reflected light filtered through an optical filter whose wave lengths are distributed around a medium wave length approximating to the wave length corresponding to the object's normal unmodified color. Provision may also be made for the light emitter to comprise an optical filter emitting a light whose spectral distribution is at least approximative to that corresponding to the sensitivity of the human eye. The signal processing detector cricuit in such cases comprises a peak detector comprising an analogue memory. The peak detector is connected to the input of an analogue/digital and digital analogue converter whose output feeds the display unit. The display unit comprises: a volt meter; and a signal proportional to the output signal of the peak detector (the proportionality coefficient being less than 1) wherein and whereby there is compared in a comparator, with the output signal of the photo transducer and the comparator initiating, at the moment the two compared signals are equal, resetting to zero of the said converter as well as the start of a first timed period. At the end of this interval, the peak detector is reset to zero whereupon a second timed period is started. At the termination of said second timed period, the display unit is reset to zero.

Apparatus according to the present invention has the advantage of being extremely simple to handle. This comes about by virtue of the fact that it suffices to bring the optical emitter-receiver fiber bundles near the object to be investigated until they coincidentally happen to (unnecessarily) come into contact with the object or, as is more predominently experienced, in the immediate proximity of any such actual contact if and when such contact must be avoided. In any case, whether contact with the object is established or not, the measurement is effected before the said contact takes place. Thus, the measurement is not disrupted or invalidatingly thrown off by any possible disturbing effect of the contact of the optical fiber on the object whose color properties and characteristics are being evaluated and determined.

The result of the measurement is numerically displayed on a digital voltmeter. As indicated, this voltmeter is automatically reset to zero after a certain display period. This then makes possible to effect a great number of measurements in an extremely short time. Moreover, it should be observed that the measurement effected only concerns an extremely limited zone of the object investigated. As has been mentioned, it is completely independent of the coloration of the object's surrounding zones. Thus, there is no longer dependence on the ability of the human eye to take into account the colorimetric data of the surroundings of the zone subjected to observation. The apparatus supplies a color determination for a given filtering of the returned luminous emission. Of course, the numerical value obtained is modified if the spectral characteristics of the light emission or of the filtering are changed. On the other hand, the results which can be obtained by the apparatus and the technique of the present invention are much more independent of the luminous emission if a color modification is studied. In other words, if one effects a measurement on a zone of the object under color investigation and evaluation and compares the results of that with a similar measurement made on the same object with the same luminous emission (either at the same point of at a different point after the color of the observed zone has been modified), excellently good and close comparison values are generally obtained.

In the special case where the apparatus is used for an investigation of the human (or other animal) skin, it is preferable to use an optical filter giving a maximum intensity in yellow and whose total range is in the visible spectrum. In these conditions, the maximum response of the apparatus is obtained by examining a yellow object. Due to this, the examination of normal human skin, for example, allows approximately 70% to 80% of the maximum response to be obtained. If erythemas of the skin are studied, as will be seen as an expectable generality that: the redder the skin, the lower the numerical value can be anticipated to be obtained. And, when a pronounced erythema is involved, the reception value of the sensor is approximately 10 to 20% of the maximum response of the said sensor.

ADVANTAGES OF INVENTION COMPARED WITH PRIOR ART

As is clearly evident in the foregoing, there are prominently evident amongst the beneficial features of practice of the present invention (i) possibility of working in restricted zones; and (ii) instantaneous measurement capability.

In contrast, with this and as an illustration thereof, the disclosure and showings of such prior art as represented in the aforementioned U.S. Pat. No. 4,278,353 do plainly and unequivocally teach and direct the necessity of operation of the patented device at a significant distance from the point (of viewing) where maximum output signal is produced. This is particularly brought out at Column 4, Lines 49-50 of the said Reference, which unmistakably spells out that "it is desirable to operate at the spacing producing maximum output."

Collated to this, the disclosure of the above-mentioned Kolmel et al reference is also notable in being directed to the study of erythema and pigmentations. It suggests use of a device which sends light through a telescope T from a light conduct L onto the object M. The light returned by the object (or subject being studied) is collected in a circular mirror R, wherefrom it is transmitted to a photodetector. The head of the Reference "R" device can be perpendicularly moved with respect to the subject being investigated.

However and notwithstanding, the above-discussed device of Kolmel et al reference has gross lacks and deficiencies as regards the possibility of its performance of what can be done in and by practice of the present invention. These, namely and to wit, are:

(A) The Kölmel et al device brings about an alternative vertical displacement as a result of operation of a motor above the surface being measured. This enables detection of the maximum light received during the course of the continuous movement so engendered. To the contrary, the device of the present invention makes an instantaneous measurement while falling onto the surface to be measured or being brought into manual contact therewith (or, in other words, by being there placed). It is evident that the present technique according to the instant innovation requires utilization of some sort of electronic memory device for satisfactory usage and results therewith. There is no mention of any such thing in said Kölmel et al Reference.

(B) The presently-contemplated apparatus, as is clear, works instantaneously by placement thereof on any part of the body (or other surface) to be tested; this capability imbuing it with an ease of use notably absent in anything fairly derivable from the said Kölmel et al Reference. Moreover, and as is readily apparent, no device possible to contrive from the disclosure and teachings of Kölmel et al could possibly work in zones or upon areas that are either hidden or difficult to reach, or both (as in examination of the nose, throat, ears and/or other body cavities, etc.).

(C) Furthermore, the Kölmel et al Reference apparatus functions from a light which has been *diffused* by the object undergoing study. There is no other way to embody a device pursuant to Kölmel et al if its permissible teachings and directions are to be observed by anyone with ordinary and merely routine skill in the art! To the contrary and with practical meaning thereabout insofar as concerns benefits and advantages flowing therefrom, practice of the present invention is made by operation with a reflected light.

(D) In embodimentations of the instant invention, and in great contradistinction to what is involved in the following of said Kölmel et al Reference, the emitting and receiving (of light) are interdependent and bring about the same movement—this, as indicated being quite and materially and significantly different from what is involved in the practice of anything perceptible in the Kölmel et al taught in Reference (wherein, as has been pointed out, only the reception is moved.)

It is thus easy to see that what is involved in the present invention is very much and most importantly differentiable over and clearly distinguishable from anything prejudicially-derivable thereagainst in and from said Kölmel et al Reference.

Along with the foregoing, U.S. Pat. No. 3,327,584 merely describes the use of optical emitting-receiving coaxial fibers. The existance of these is well known to the art. However, nothing in U.S. Pat. No. 3,327,584 suggests utilization of such products in any device along the lines suggested by the Kölmel et al Reference (they being, in this light and purview, merely an abstract "nut" not intended or suggested for use or combination with a given specific and particularized "bolt.") And, nothing in the Kölmel et al Reference makes even the remotest of suggestions of hints that such a sophisticated coaxial fiber could be utilized in any way in the therein-contemplated contrivance.

The identified and above-discussed U.S. Pat. No. 4,278,353 does describe the use of optical emitting-/receiving fibers in a described preferable form of operation wherein conduction of the procedure is done at some considerable distance from the point at which the maximum signal is produced. However, this Patent, the U.S. Pat. No. 3,327,584 like Reference, does not foresee or suggest that any measurement will be possibilitated by light falling on the object to be examined so as to thus assure maximum memorization which avoids the handicap and limitation(s) of having to involve or assure any difficulty in operational positioning.

As has been amply brought forth, the present invention, as is abundantly perceivable, pertains specifically in the field of and for the detection of a maximum signal supplied by the photoreceptor during the course of movement of the extremity of the collector fiber. No such concept is even remotely perceptible in the heretofore-available prior art.

PARTICULARIZED DESCRIPTION OF THE INVENTION

In order that the present invention may be more readily understood, an embodiment represented on the accompanying Drawing will now be described. This, needless to mention, is only by way of a purely illustrative and non-restrictive exemplification. In the Drawing:

FIG. 1 represents the curves giving luminuous intensity L returned by the object (and picked up by the photo receiver) for a given luminous emission in relation to distance "d" between the object and the end of the optical fibers of the emitter-receiver assembly used in the apparatus according to the invention, with each one of these curves corresponding to a different color of the object subjected to examination.

Figure 2:
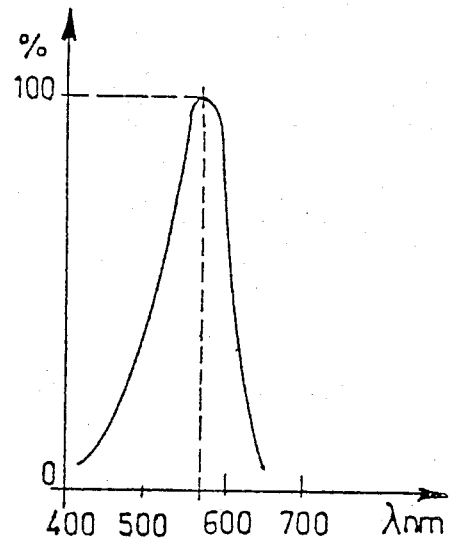
FIG. 2 represents the distribution of the spectrum obtained by means of the optical filter which is interposed ahead of the photo receiver of the preferred embodiment of apparatus.

Referring now more specifically to the Drawing, there will be seen the emitter-receiver unit 1 of the apparatus according to the invention. Unit 1 comprises a light bulb (which emits a white light) and an optical filter whose spectral characteristics are represented by the curve of FIG. 2. The luminous beam is sent into an emitter optical fiber bundle which constitutes at its end surface 6 the sheath of a second optical fiber bundle which is coaxial with the first. The two coaxial, optical fiber bundles have a common end surface 6. The second bundle serves as a receiver which is intended and adapted to receive the luminous flux originating from the emitter optical fiber bundle. The second optical fiber bundle or receiver bundle is connected to a photo transducer of the apparatus according to the invention. The emitter-receiver unit 1 is not described in greater detail since these are readily available. As such a unit it is marketed by the "SKAN-A-MATIC" Company of the United States of America under its Catalogue Reference Number "S 35203," with the optical filter.

In view of the involved geometry in and of the optical fiber bundles, the light emitted by the peripheral emitter fiber bundle and returned by the object under investigation only enters the optical receiver fiber bundle under certain angular pre-conditions. In this way, the light intensity detected by the photo transistor which is connected to the receiver fiber bundle passes through a maximum when the common ends of the emitter and receiver fiber bundles are located at a distance "D" (FIG. 1) from the object being investigated.

Figure 1:
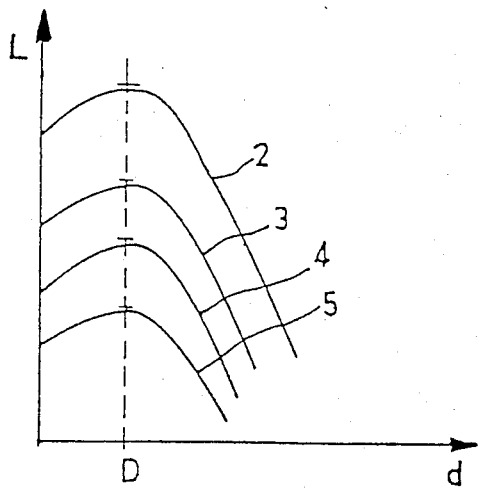

FIG. 1 shows the shape of the curve indicating light intensity "L" as is determined by the photo receiver in relation to distance "d" from the front end surface 6 of the optical fiber bundles in relation to the object. Distance "D", corresponding to the maximum value of the light reception, is always the same for a given emitter-receiver unit 1.

The different curves represented in FIG. 2 of the Drawing show the light intensities received by the photo transistor. These are in accordance with the color of the object which is presented in front of the end surface 6 of the emitter-receiver bundle assembly. If this object under examination has a color whose wave length corresponds to the maximum of the spectral distribution of the particular filter selected, the light intensity detected by the photo transistor is the maximum one which corresponds to curve 2 of FIG. 1.

On the other hand, the more that the color of the object being examined differs from the dominant color of the filter, the lower is the light intensity detected by the photo transistor. Curves 3, 4, and 5 show the light reception levels for orange, orange-red, and red objects. At the same time, Curve 2 responds to a yellow object. As will be clear from the wave lengths indicated in FIG. 2, the involved filter is centered on a yellow color.

The values of the maxima of Curves 2, 3, 4 and 5 therefore constitute a determination of the color of the object which is presented opposite the end surface 6 of the coaxial optical fiber bundles. Of course, the numerical values corresponding to these maxima depend essentially on the nature of the filter which has been used for and in the course of their determination. On the other hand, if a given object changes its color and if the same apparatus is used to effect measurements both before and after the color modification, comparison of the results of the two measurements will give a determination of the color modification. Such a modification determination depends to a far lesser degree on the nature of the light emission used than when other procedures are employed.

To effect the measurement, it is sufficient to bring the end surface 6 of the coaxial optical fibers near to the object. This may involve movement of end surface 6 object (especially if these is nothing prohibiting contact) or up to a proximity of generally no more than a few millimeters if contact with the object must be avoided. In the course of this approach, the photo transistor output signal passes through a maximum at the moment when the end of the optical fibers is at a distance "D" from the object. As will be described in detail below, the apparatus allows the measurement to be effected at the precise moment when the distance "d" passes the distance value "D".

This technique is particularly worthwhile if it is intended to study erythemas of the skin. This is because, in such a case, it is possible to bring the end surfaces of the optical fibers right up to contact with the skin, despite the fact that this contact will cause the skin to whiten and will therefore modify the color of the observed zone. Nonetheless and notwithstanding, this is of no practical moment or consequence, since the measurement is taken at a moment before the actual contact has been effected and at a time, therefore, when the skin still retains its unmodified color.

Figure 3:
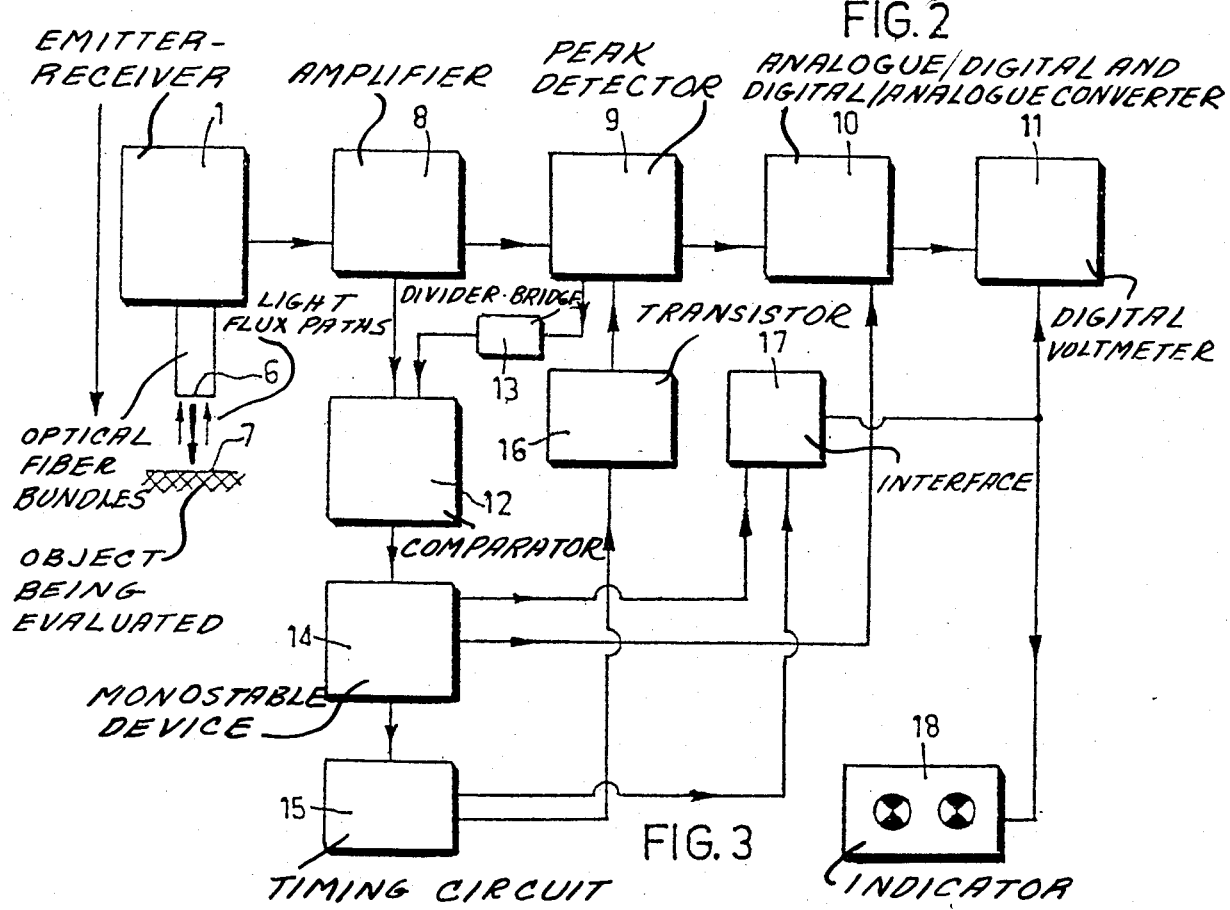
FIG. 3 is a block diagram of the electronic circuit processing the output signal of the photo receiver of the apparatus according to the invention.

In FIG. 3 of the Drawing, there has been shown the block diagram of the electronic circuit which allows the measurement to be obtained at the moment when end surface 6 of the optical fiber bundles is located at the distance "D" from object 7 being investigated. The output signal of the photo transistor of the emitter-receiver unit 1 is sent to an amplifier 8 whose output is applied as input to a peak detector 9. In the conventional manner, the peak detector 9 comprises a capacitor having a sizable time constant (typically about 10 seconds, for instance), since this capacitor discharges only very slowly.

Figure 4:
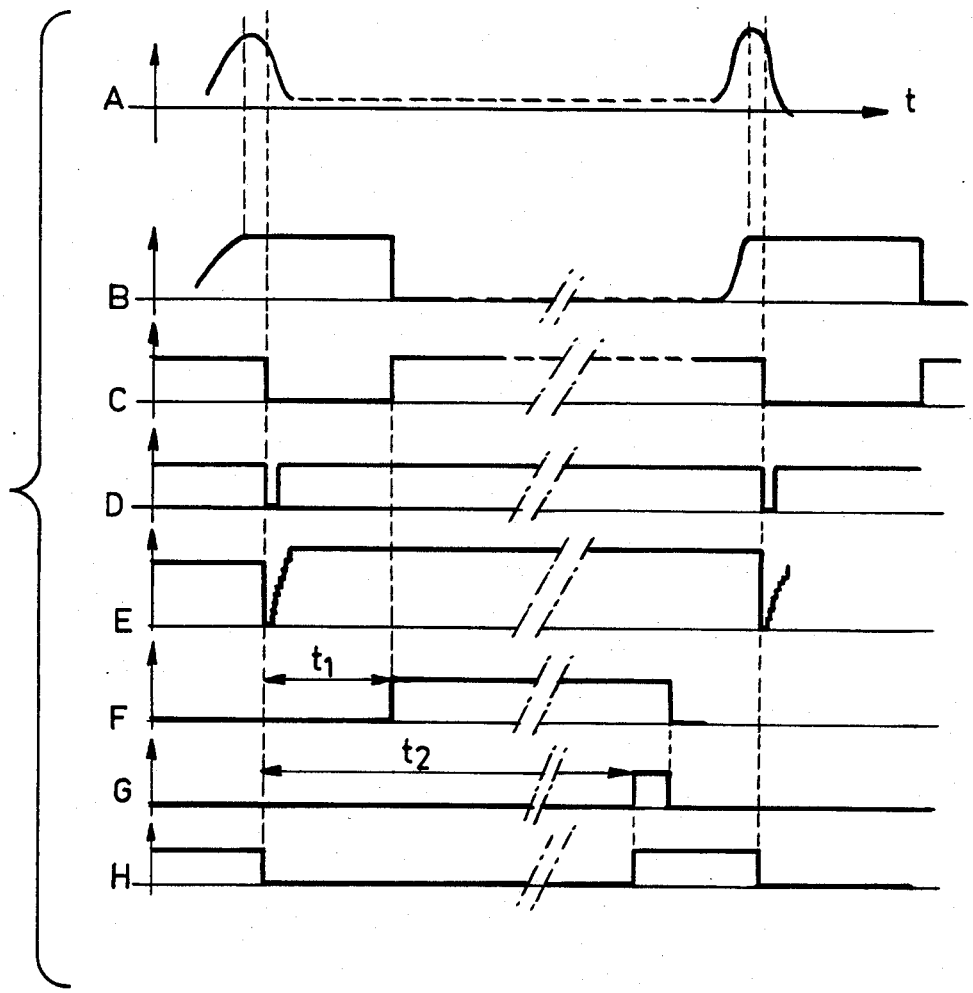
FIG. 4 represents the formation, with respect to time, of the signal at various points of the block diagram of FIG. 3.

The output signal of amplifier 8 is represented on line A of FIG. 4 for the part which corresponds to the passage of the photo transducer output through the maximum, i.e. at a moment when end surface 6 of the optical fibre bundle is at a distance "D" from object 7. The signal supplied at the output of peak detector 9 is represented on line B of FIG. 4 of the Drawing.

The above-mentioned supplied signal is directed to an analogue/digital and digital/analogue converter 10. When reset to zero, the converter 10 charges a memory at the frequency of its internal timer and converts the memory content into an analogue output voltage. And, it also compares the output voltage with the input voltage. The charging of the digital memory continues until the output voltage is equal to the input voltage. At this moment, converter 10 is blocked until it receives a reset pulse causing it to reset to zero. The output voltage supplied by converter 10 is applied to a digital voltmeter 11 which constitutes the display unit.

The output from amplifier 8 is also applied to a comparator 12, whose second input receives the voltage corresponding to the output of peak detector 9 which is reduced by a proportionality coefficient of less than 1 derived from a divider bridge 13. In this embodiment, the proportionality coefficient selected is 0.75. The output of comparator 12 is thus a binary signal. This signal is at the higher level while the output voltage of amplifier 8 is higher than that supplied by divider bridge 13. The involved signal changes over to a lower level as soon as the opposite output voltage situation occurs.

The above-discussed binary signal from comparator 12 is represented on Line C of FIG. 4. The descending front of the signal on Line C therefore indicates that the maximum of the output signal of the photo transistor of unit 1 has been passed and that one may therefore charge the converter 10 with the value stored in peak detector 9. The use of a proportionality coefficient of 0.75, by virtue of the divider bridge 13, makes it possible to avoid any possible interference effects.

The output of comparator 12 controls a monostable device 14 whose output signal is represented in Line D of FIG. 4. The output signal of the monostable device 14 is applied to the converter 10. This signal constitutes the reset signal which serves to reset the converter to zero so as to allow the digital memory of the converter to be charged at its internal timer frequency. The charge involved is produced at the longest, within 150 nano-seconds. As explained above, when the output voltage of converter 10 is equal to the input voltage, converter 10 becomes blocked so that the display on voltmeter 11 remains constant (this display having changed during the changing time of converter 10.) The output signal of converter 10 has been represented on Line E of FIG. 4. But, in this representation, the charging time of the converter has been greatly exaggerated to make it realistically visible in the Drawing.

The monostable device 14 releases a timing circuit 15 which supplies two timed periods.

The first timed period is determined by a signal represented on Line F if FIG. 4. At a time $t_1$ after the descending front of the pulse from the monostable device 14, the signal of the first timed period has a rising front which is directed to a transistor 16 arranged in parallel with the capacitor of peak detector 9. The first timed period signal thus produces the resetting to zero of the peak detector output. This does not affect the output of converter 10, since the converter has been blocked after completing its charging. The resetting to zero of the output of peak detector 9 also prompts change to the higher level of the output of comparator 12. In the described illustration, time $t_1$ is approximately 20 ns.

The second timed period signal is represented on Line G of FIG. 4. This signal has a rising front at time $t_2$ after the descending front of the pulse produced by the monostable device 14. This rising front initiates by way of interface 17, the resetting to zero of the digital voltmeter 11, the output signal of interface 17 being represented on Line H of FIG. 4.

The second timed period signal constitutes a rectangular pulse. Its descending front entails the resetting to zero of the signal relating to the first timed period. The signal supplied by interface 17 is therefore at its lower level during a timed period $t_2$, and $t_2$ is advantageously chosen at the order of 20 seconds. This time period allows the user of the apparatus to have the display of the measurement for 20 seconds on the involved digital voltmeter 11. After these 20 seconds, the display of digital voltmeter 11 is reset to zero. An indicator device 18 is also provided to indicate by and with only one illuminated sign that the apparatus is in the measurement or "reading off" phase and, by means of a different illuminated sign, that the apparatus is on standby. This condition, as is evident, makes it possible to effect a new and subsequent measurement with the apparatus.

It will be seen that the apparatus (as well as the technique accompanying its use) which has just been described is simple to make and utilize. Thus, the overall cost price involved for both apparatus availability and use is relatively limited. Moreover, and as has been shown, the here contemplated apparatus is very simple to use. And the measurements effected can be taken very rapidly. The rapidity of these measurements makes it possible to study the kinetics of a change in colour which may for example need merely extend over several minutes.

What is claimed is:

1. Apparatus for making numerical-determination of one of the colors or of a change in a given color of an object, which apparatus is comprised of:
   (a) a source of light to irradiate the object whose numerical-determination of color is desired and to be found;
   (b) a photo transducer measn to pick up the light returned by the object;
   (c) optical fiber receiving means to direct the light returned by the object to the said photo transducer means; with
   the said optical fiber receiving means having an end that is displaceable substantially perpendicularly to the said object being investigated whose numerical-determination of color is desired and to be found in order to obtain such desired determination;
   (d) optical fiber emitter means having an end to direct the emission of said light source to a said object being investigated, said optical fiber receiving means and said emitter means being coaxially disposed at least at said ends to provide coaxial ends and to provide first and second optical fiber bundles; with
   said optical fiber emitter means and said optical fiber receiving means being disposed as a unit to be passed within and to make traversing entry substantially perpendicularly into a zone of access wherein is located the object to be investigated;
   (e) signal processing means for determining the value of the maximum of the signal supplied by the photo transducer means during the displacement of the said optical receiver means; with said signal processing means including means to provide said maximum signal value determination substantially instantaneously at the time during displacement of the said end of the optical receiving means when said receiving means is at least in very near maximum signal-generating proximity of contact with said object to be investigated; and
   (f) a display unit responsive to said signal processing means for substantially instantaneously displaying information according to the determination made; with
   (g) means associated with said apparatus assembly for moving said coaxial ends of said first and second optical fiber bundles in said unit towards and away from said object.

2. Apparatus according to claim 1, wherein:
said optical fiber emitter means and optical fiber receiver means comprise first and second optical fiber bundles having coaxial ends in the same plane substantially parallel to the object,
the said ends being displaceable together substantially perpendicularly to the object to the effect the desired determination.

3. Apparatus according to claim 1, wherein:
the said photo transducer means further comprises an optical filter.

4. Apparatus according to claim 3, wherein:
said optical filter has a spectral distribution which approximates to that which corresponds to the sensitivity of the human eye.

5. Apparatus according to any one of claims 1-4, inclusive, wherein:
said signal processing means includes a peak detector means and an analogue memory.

6. Apparatus according to claim 5, wherein:
said signal processing means further includes
an analogue/digital and digital/analogue converter having an output which feeds said display unit and an input which feeds said display unit and an input connected to the said peak detector means.

7. Apparatus according to claim 6, wherein:
said display unit comprises a voltmeter.

8. Apparatus according to claim 6, wherein:
said signal processing means further includes means to obtain a signal proportional to the output signal of said peak detector means, and means establishing a proportionality coefficient being less than 1; and
comparator means comparing the said proportional signal and the output signal of said photo transducer means whereby and wherein
as soon as the two compared signals are equal, said comparator initiates the resetting of the converter to zero as well as the start of a first timed period at the end of which there is produced a resetting to zero of said peak detector and the commencement of a second timed period at the end of which said display unit is reset to zero.

9. Apparatus according to claim 7, wherein:
said signal processing means further includes means to obtain a signal proportional to the output signal of said peak detector means, the proportionality coefficient being less than 1; and
comparator means comparing the said proportional signal and the output signal of said photo transducer means whereby and wherein
as soon as the two compared signals are equal, said comparator initiates the resetting of the converter to zero as well as the start of a first timed period at the end of which there is produced both a resetting to zero of said peak detector and the commencement of a second timed period at the point of which said display unit is reset to zero.

10. Apparatus according to any one of claims 1-4, which is usable for examining the skin, wherein
said light source is one which emits light practically completely in the visible spectrum with a maximum in yellow.

11. Apparatus according to claim 5, which is usable for examining the skin, wherein
said light source is one which emits light practically completely in the visible spectrum with a maximum in yellow.

12. Apparatus according to claim 6 which is usable for examining the skin, wherein:
said light source is one which emits light practically completely in the visible spectrum with a maximum in yellow.

13. Apparatus according to claim 7 which is usable for examining the skin, wherein:
said light source is one which emits light practically completely in the visible spectrum with a maximum in yellow.

14. Apparatus according to claim 8 which is usable for examining the skin, wherein:
said light source is one which emits light practically completely in the visible spectrum with a maximum in yellow.

15. Apparatus according to claim 9 which is usable for examining the skin, wherein:
said light source is one which emits light practically completely in the visible spectrum with a maximum in yellow.

16. A process for making a numerical determination of one of the colors, and a change in a given color, of an object which comprises the Steps of:

(I) taking an apparatus characterized in therein having
  (a) a source of light to irradiate the object whose numerical-determination of color is desired and to be found;
  (b) a photo transducer means to pick up the light returned by the object;
  (c) optical fiber receiving means to direct the light returned by the object to the said photo transducer means; with
  the said optical fiber receiving means having an end that is displaceable substantially perpendicularly to the said object being investigated whose numerical-determination of color is desired and to be found in order to obtain such desired determination;
  (d) optical fiber emitter means having an end to direct the emission of said light source to a said object being investigated, said optical fiber receiving means and said emitter means being coaxially disposed at least at said ends to provide coaxial ends and to provide first and second optical fiber bundles; with
  said optical fiber emitter means and said optical fiber receiving means being disposed as a unit to be passed within and to make traversin entry substantially perpendicularly into a zone of access wherein is located the object to be investigated;
  (e) signal processing means for determining the value of the maximum of the signal supplied by the photo receiver (b) during the displacement of the said end of the optical receiver means (c); with
  said signal processing means for determining the value of the maximum of the signal supplied by the photo transducer means during the displacement of the said optical receiver means; with said signal processing means including means to provide said maximum signal value determination substantially instantaneously at the time during displacement of the said end of the optical receiving means when said receiving means is at least in very near maximum signal-generating proximity of contact with said object to be investigated; and
  (f) a display unit responsive to said signal processing means for substantially instantaneously displaying information according to the determination made; and therewith
(II) moving said coaxial ends of said first and second optical fiber bundles in said receiving means and said emitter means towards the said object; while
(III) receiving the light from said light source return from the said object; then
(IV) processing the output signal of said photo transducer means using the detector circuit in said signal processing means; and
(V) displaying substantially instantaneously the output of said detector circuit in said signal processing means using for such purpose the display unit.

17. A process according to claim 16, when carried out:
using an optical filter in the path of the said returned light picked up from the illuminated object,
said optical filter having a medium wave length which approximates to the wave length corresponding to the normal unmodified color of the object being investigated.

* * * * *